United States Patent [19]

Simmons

[11] Patent Number: 5,895,354
[45] Date of Patent: Apr. 20, 1999

[54] INTEGRATED MEDICAL DIAGNOSTIC CENTER

[76] Inventor: Paul L. Simmons, 8825 Laurel Dr., Pinellas Park, Fla. 33782

[21] Appl. No.: 08/882,201

[22] Filed: Jun. 25, 1997

Related U.S. Application Data

[60] Provisional application No. 60/020,625, Jun. 26, 1996.

[51] Int. Cl.⁶ .................................................. A61B 5/00
[52] U.S. Cl. ...................... 600/301; 600/300; 600/494; 128/903
[58] Field of Search .................... 128/903; 600/300, 600/301, 494; 5/600, 136, 159.1, 160, 161

[56] References Cited

U.S. PATENT DOCUMENTS

| | | | |
|---|---|---|---|
| 4,998,534 | 3/1991 | Claxton, III et al. | 600/494 |
| 5,441,047 | 8/1995 | David et al. | 600/301 |
| 5,621,930 | 4/1997 | Reppas et al. | 5/136 |
| 5,701,904 | 12/1997 | Simmons et al. | 600/301 |

*Primary Examiner*—Robert L. Nasser
*Assistant Examiner*—Michael Astorino
*Attorney, Agent, or Firm*—A. W. Fisher, III

[57] ABSTRACT

An integrated medical diagnostic center configured to provide emergency communications, immediate measurement of various physiological conditions and provision for administration of emergency treatment, the integrated medical diagnostic center comprising a cabinet including a plurality of compartments to house an emergency communications device, a plurality of physiological diagnostic devices, at least one patient support movable between a stored position and an operative position and at least one emergency treatment device.

29 Claims, 7 Drawing Sheets

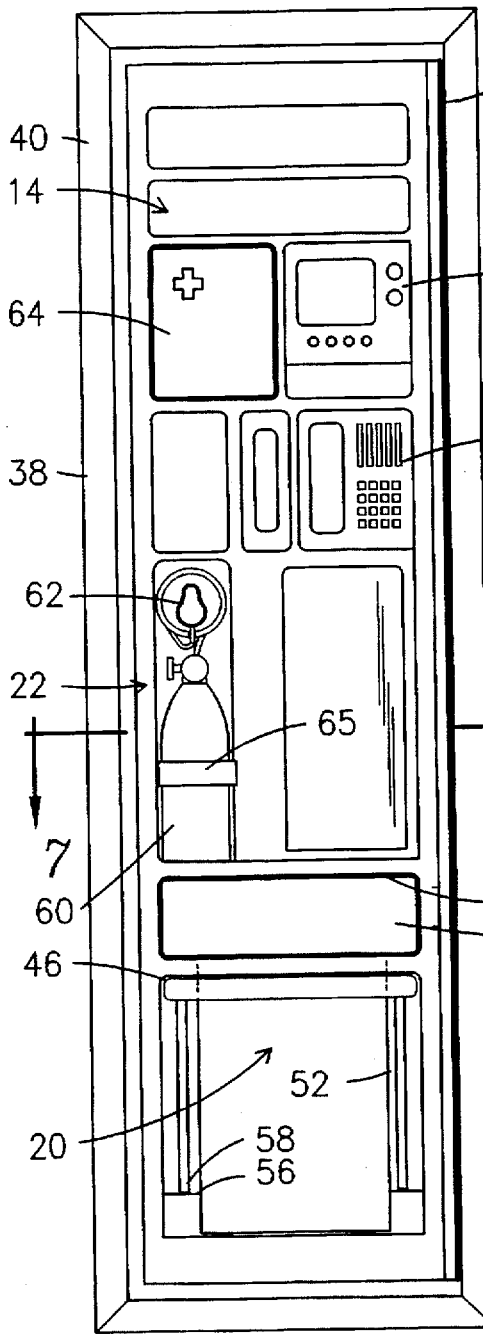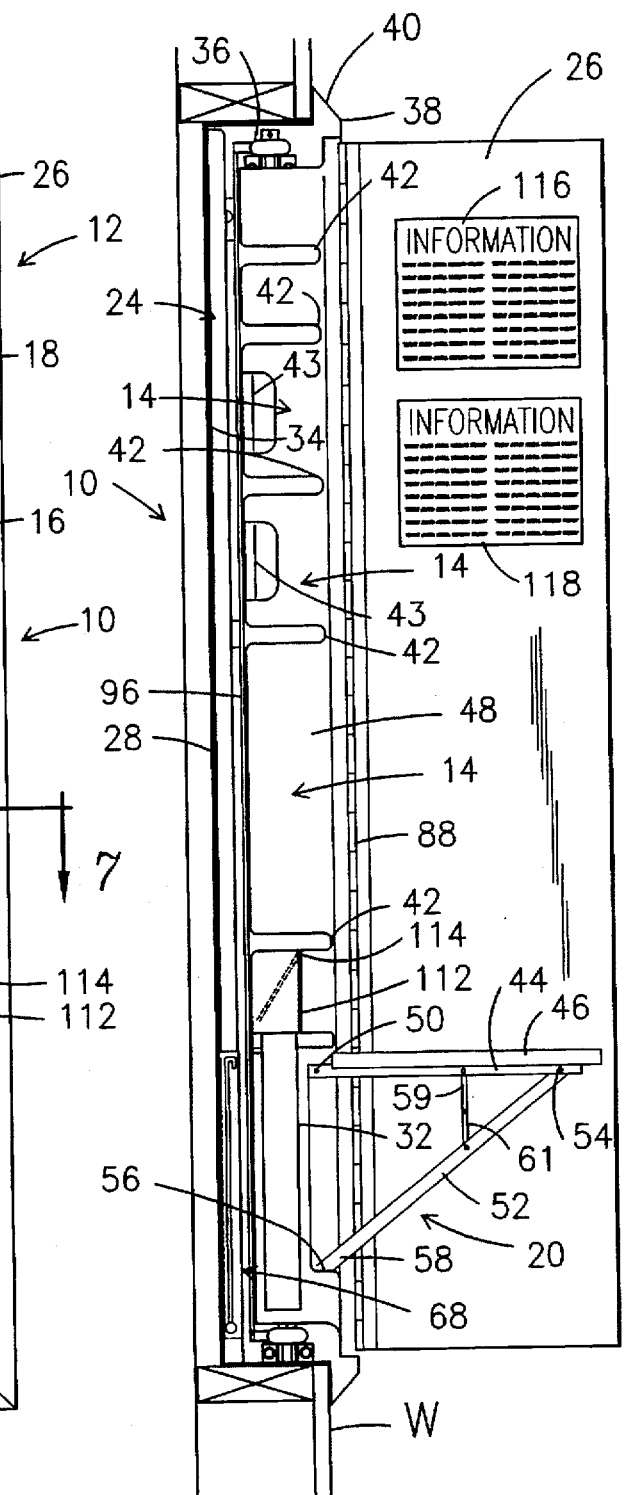
Fig. 3
Fig. 4

INTEGRATED MEDICAL DIAGNOSTIC CENTER

CROSS REFERENCE

This is a regular application of patent application claiming priority and converting from the provisional application filed Jun. 26, 1996 assigned application number 60/020,625.

BACKGROUND OF THE INVENTION

1. Field of the Invention

An integrated medical diagnostic center configured to provide emergency communications, immediate measurement of various physiological conditions and provision for administration of emergency treatment.

2. Description of the Prior Art

It has long been recognized that in a medical emergency survival of a person in trauma is often dependent upon immediate diagnosis and interim emergency treatment.

Unfortunately, most homes, offices and public places such as department stores, malls, restaurants, theaters, schools, health clubs, factories, warehouses, nursing homes and the like are not equipped with means to provide immediate emergency diagnosis and interim treatment for such traumas such as heart attack, stroke, seizure, concussion, dieting trauma, exercise exhaustion or diabetic shock.

Thus there is a need for a self-contained integrated diagnostic treatment center to monitor and determine one's physical condition and when necessary to provide emergency equipment to maintain life support functions until emergency medical personnel are available.

SUMMARY OF THE INVENTION

The present invention relates to an integrated medical diagnostic center configured to provide emergency communications, immediate measurement of various physiological conditions and means for administration of emergency treatment.

The integrated medical diagnostic center comprises a cabinet movable between a closed and open position including a plurality of compartments to operatively house an emergency communications such as a preprogrammed speaker phone, a plurality of diagnostic devices such as a blood glucose monitor kit, thermometer or blood pressure and pulse monitor, a first patient support movable between a stored position and an operative position, at least one emergency treatment device such as an oxygen tank and mask combination, a second patient support movable between a stored position and an operative position, a cabinet door and a cabinet positioning means.

The first patient support comprises a seat platform pivotally coupled to the cabinet and a pair of seat supports coupled to opposite sides of the seat platform. Support ledges are formed on the lower portion of the cabinet to selectively receive and support the free ends of the seat supports to maintain the seat platform in the operative or horizontal position.

The second patient support comprising a platform is pivotally coupled to the cabinet and a pair of outer platform supports. A foot element is attached to the free ends of the platform supports to maintain the platform in the operative or horizontal position.

The positioning means comprises an upper and lower positioning assembly coupled together by a first and second substantially vertical interconnecting member to pivotally mount the cabinet to a stud. The upper and lower positioning assembly each comprises a substantially L-shaped hinge member coupled between a first pivot pin coupled to a hinge element affixed to the wall stud and a substantially horizontally disposed flat hinge element by a second pivot pin that is, in turn, pivotally coupled to the cabinet and mounting plate by a third pivot pin. The substantially L-shaped hinge members are interconnected by the first substantially vertical interconnecting member; while, the substantially horizontally disposed flat hinge elements are interconnected by the second substantially vertical interconnecting member. The three pivot points allow the cabinet to be stored in the recess formed in the wall substantially parallel to the wall and positioned substantially perpendicular to the wall when in use.

The integrated medical diagnostic center is disposed in the recess. To use, the cabinet door is opened to permit access to the emergency communications device, the diagnostic devices and the first patient support. With the cabinet in the first position or intermediate position, the first patient support is opened or deployed to the operative position with the pair of seat supports placed in the support ledges formed on the opposite sides of the lower portion of the substantially vertical interior wall of the cabinet to support the free ends of the seat supports to maintain the seat platform in the operative or horizontal position.

With the person seated on the seat platform, the diagnostic devices and the emergency treatment devices are accessible for use on the patient. With the cabinet in the open position, the second patient support may be deployed or moved to the operative position such that the foot elements maintain the platform in the operative or horizontal position to allow the person to lie prone on the second support.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature and object of the invention, reference should be had to the following detailed description taken in connection with the accompanying drawings in which:

FIG. 3 is a front view of the integrated medical diagnostic center with the cabinet door in the open position and the first patient support in the operative position.

FIG. 4 is a side view of the integrated medical diagnostic center with the cabinet door in the open position and the first patient support in the operative position.

Similar reference characters refer to similar parts throughout the several views of the drawings.

DETAILED DESCRIPTION OF THE PREFERRED EMBODIMENT

Figure 1:
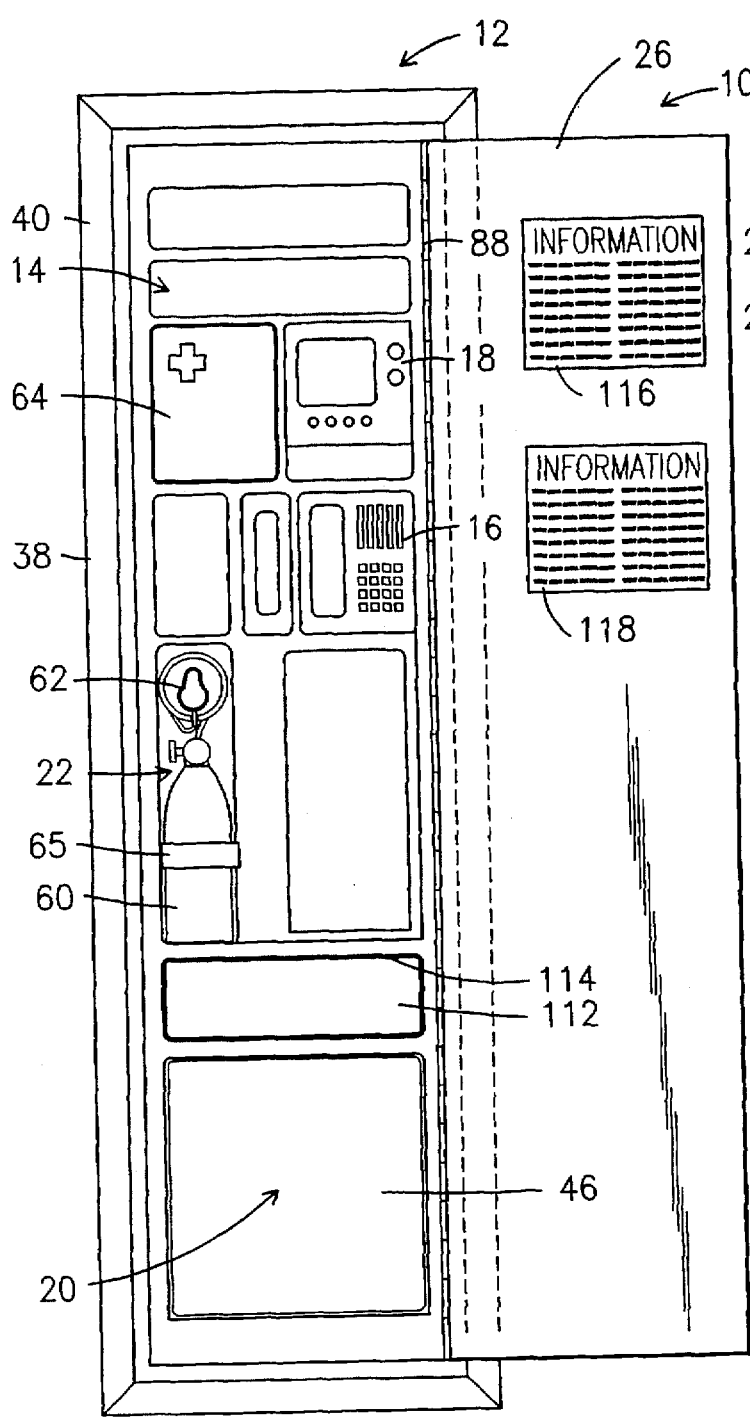
FIG. 1 is a front view of the integrated medical diagnostic center with the cabinet door in the open position.

As shown in the various drawings, the present invention relates to an integrated medical diagnostic center configured to provide emergency communications, immediate measurement of various physiological conditions and means for administration of emergency treatment.

As shown in FIGS. 1 through 5, the integrated medical diagnostic center 10 comprises a cabinet 12 movable between a closed and open position including a plurality of compartments 14 to operatively house an emergency communication device 16, a plurality of diagnostic devices each indicated as 18, a first patient support generally indicated as 20 movable between a stored position (FIGS. 1 and 2) and an operative position (FIGS. 3 and 4), at least one emergency treatment device generally indicated as 22, a second patient support generally indicated as 24 movable between a stored position (FIGS. 2 and 4) and an operative position (FIG. 5), a cabinet door 26, a substantially rectangular recess liner pan 28, a cabinet positioning means generally indicated as 30 (FIGS. 5 through 7) and a disposal container 32 (FIGS. 1 through 7).

Figure 2:
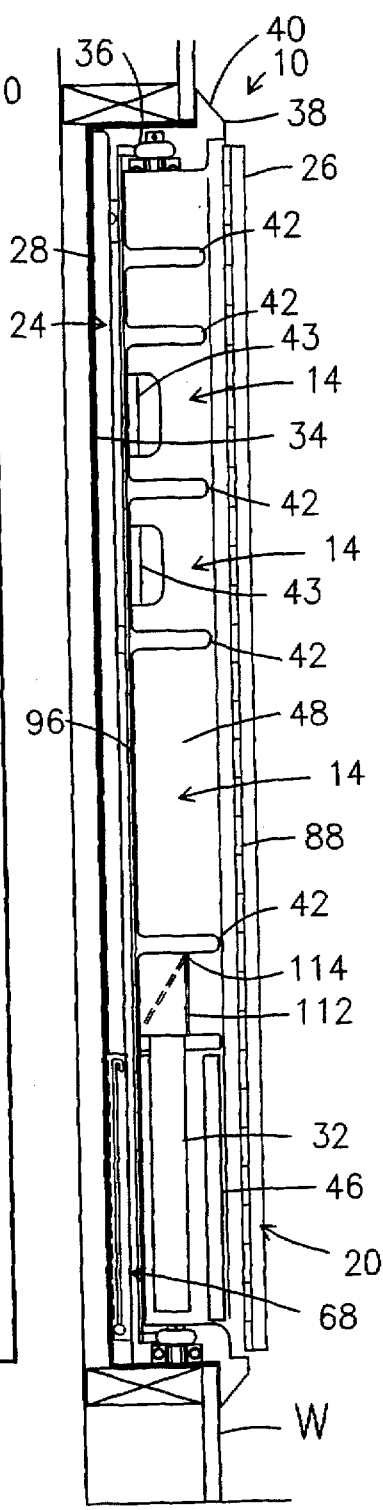
FIG. 2 is a side view of the integrated medical diagnostic center with the cabinet door in the closed position.

The cabinet 12 comprises a substantially vertical interior wall 34 with a peripheral side wall 36 extending outwardly therefrom terminating in an outer flange 38 having an inclined surface 40. The outer flange 38 engages the wall W when the cabinet 12 is in the closed position (FIGS. 2, 4, 6 and 7). A plurality of substantially horizontal elements each indicated as 42 extend outwardly from the substantially vertical interior wall 34 to cooperatively form the compartments 14 therebetween. Securing means 43 may be affixed to the substantially vertical interior wall 34 to selectively secure the emergency communications device 16, the diagnostic devices 18 and the emergency treatment device 22 within the corresponding compartments 14 (FIGS. 2 and 4). The securing means 43 may comprise a hook and loop combination or other suitable securing or attachment means.

The emergency communication device 16 comprises a state of the art pre-programmed speakerphone with a single button each to access 911, emergency room and doctor.

The diagnostic devices 18 may comprise a portable blood glucose monitoring kit requiring no timing, wiping or blotting capable of effectively measuring the glucose level within one minute, a thermometer to instantly measure temperature from the ear within one second or a blood pressure and pulse monitor such as a portable finger blood pressure and pulse monitor capable of measuring blood pressure within one minute.

As shown in FIGS. 1 through 4, the first patient support 20 comprises a seat platform 44 including a cushion 46 pivotally coupled to the vertical side walls 48 of the peripheral side wall 36 by a pivot means 50 on opposite sides thereof at the inner portion thereof and a pair of seat supports each indicated as 52 pivotally coupled to opposite sides of the seat platform 44 on the outer portion thereof by pivot means 54. Support ledges 56 are formed on the opposite sides of the lower portion of the substantially vertical interior wall 34 to selectively receive and support the free ends 58 of the seat supports 52 to maintain the seat platform 44 in the operative or horizontal position as shown in FIGS. 3 and 4. In addition, the first patient support 20 may include a first and second seat platform brace indicated as 59 and 61 respectively pivotally coupled to each other and to the seat platform 44 and at least one of the seat supports 52.

As shown in FIGS. 1 and 3, the emergency treatment device 22 may comprise a combination oxygen tank and oxygen mask indicated as 60 and 62 respectively retained in the corresponding compartment 14 by a fastening means 65 such as a strap and snap combination or a first aid kit 64.

Figure 7:
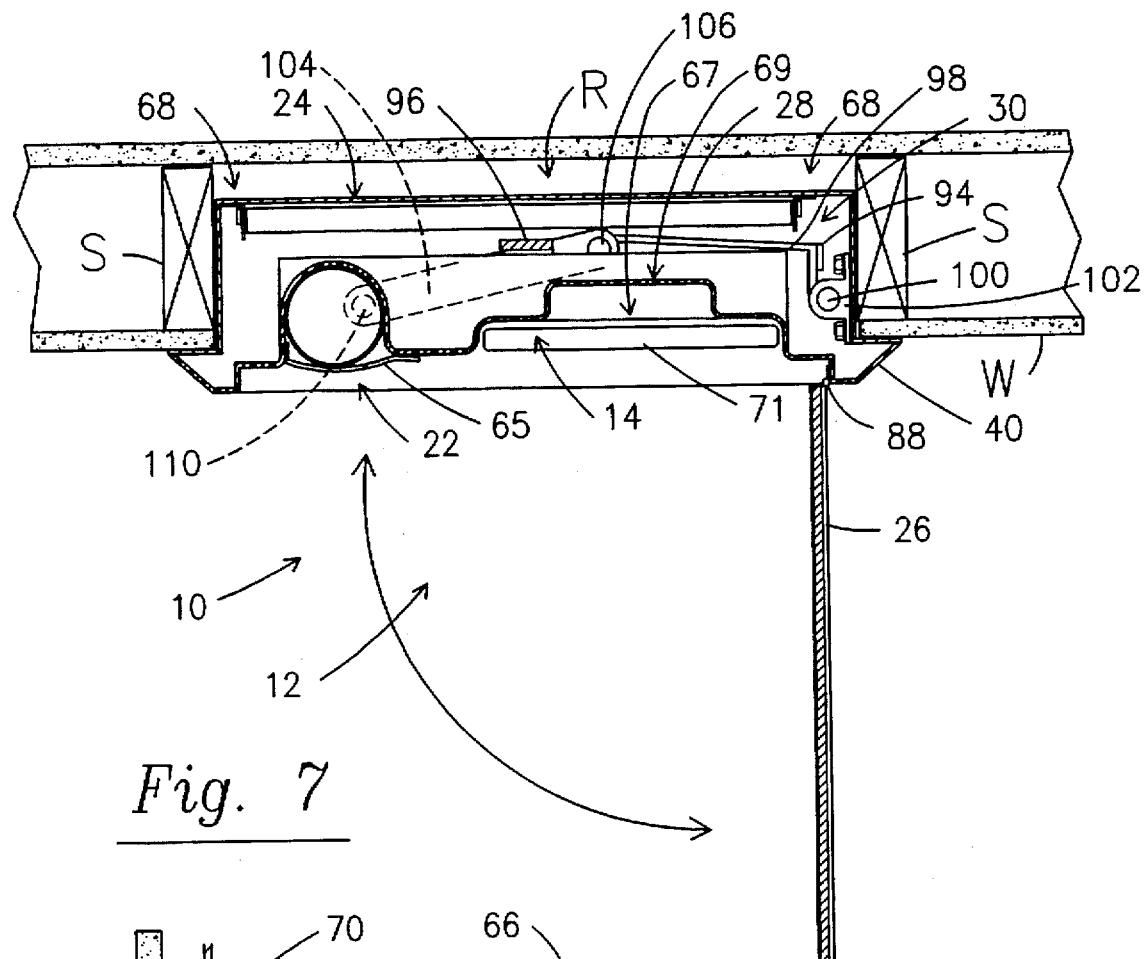
FIG. 7 is a cross-sectional top view of the integrated medical diagnostic center taken along line 7—7 of FIG. 3 with the cabinet door in the open position.
Figure 8:
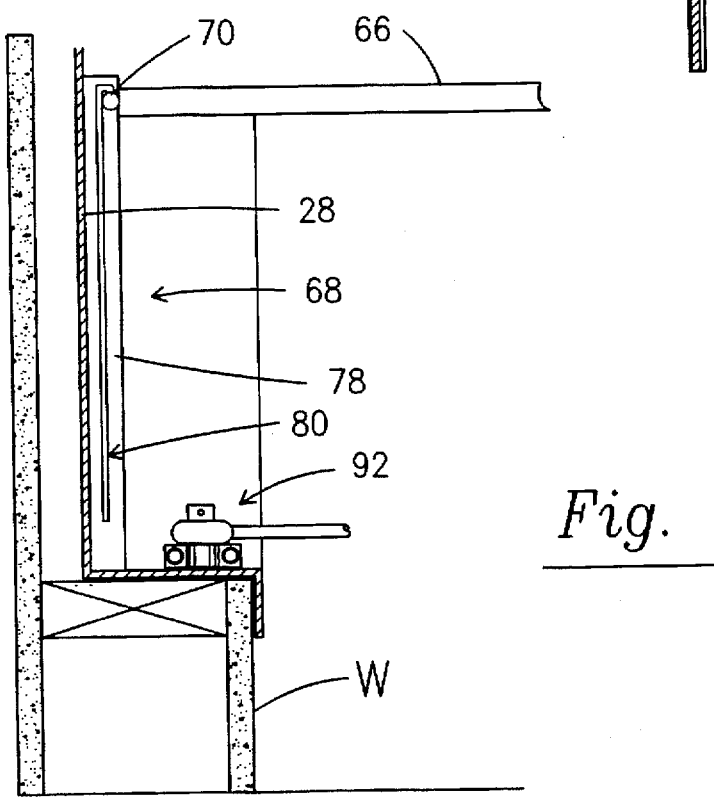
FIG. 8 is a partial side view of the integrated medical diagnostic center with the second patient support in the operative position.

As shown in FIG. 7, the emergency treatment device 22 may comprise a burn packet 67 stored in the inner recess 69 formed in the corresponding compartment 14 and a blanket 71.

Figure 5:
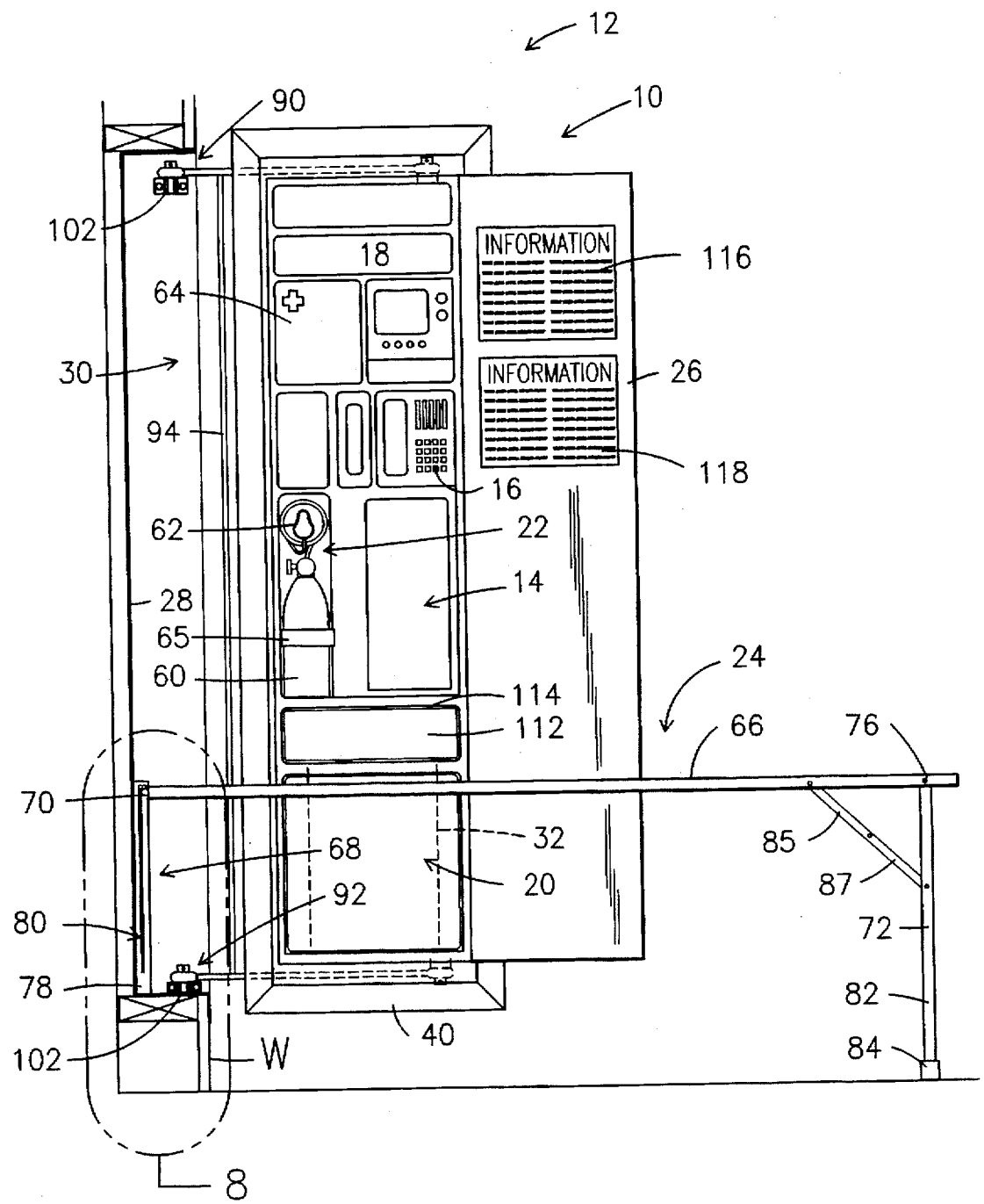
FIG. 5 is a side view of the integrated medical diagnostic center with both the cabinet door and the cabinet in the open position and the second patient support in the operative position.

As best shown in FIG. 5, the second patient support 24 comprises a platform 66 pivotally coupled to a pair of inner side supports each generally indicated as 68 by a corresponding pivot member 70 on opposite sides thereof and a pair of outer platform supports each indicated as 72 interconnected by a cross-brace 74 (FIG. 6) pivotally coupled to opposites of the platform 66 on the outer portion thereof by a pivot member 76. Each inner side support 68 comprises a substantially vertical flat support member 78 affixed to the cabinet 12 including a substantially vertical J-shaped slot 80 to receive the corresponding pivot member 70. A foot element 82 is attached to the free ends 84 of the platform supports 72 to maintain the platform 66 in the operative or horizontal position as shown in FIGS. 5 and B. As shown in FIG. 5, the second patient support 24 may include a first and second platform brace indicated as 85 and 87 respectively pivotally coupled to each other and to the platform 66 and at least one of the outer platform supports 72.

As shown in FIG. 7, the cabinet door 26 may comprise a mirror or other decorative member hingedly mounted to the cabinet 12 by a hinge 88 coupled to the cabinet 12 and cabinet door 76.

As best shown in FIG. 7, the substantially rectangular recess liner pan 28 is configured to be placed in a recess formed in the interior wall W between wall studs S.

Figure 6:
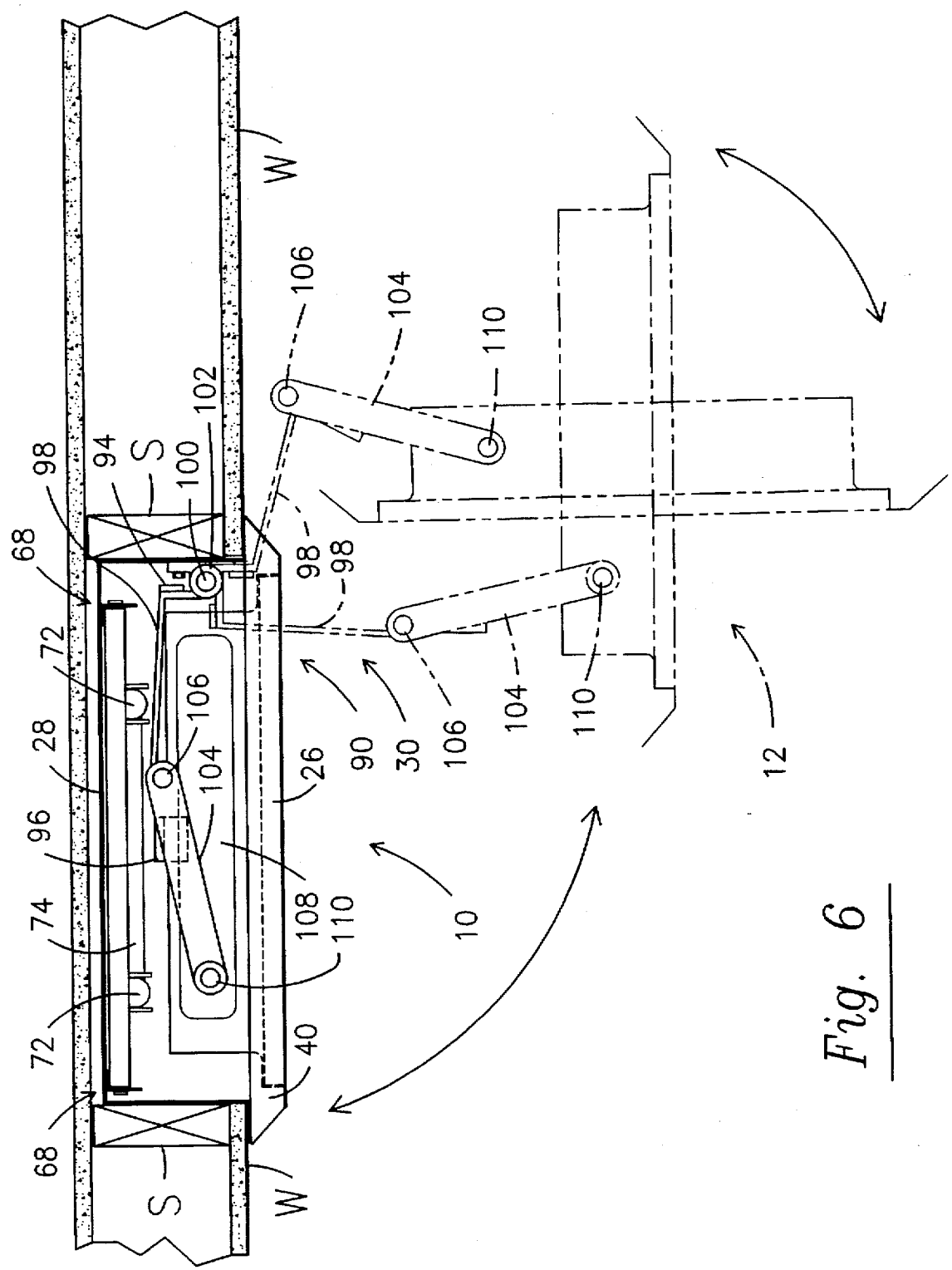
FIG. 6 is a top view of the integrated medical diagnostic center with the cabinet in various positions.

As best shown in FIGS. 5 through 7, the cabinet positioning means 30 comprises an upper and lower positioning assembly generally indicated as 90 and 92 respectively coupled together by a first and second substantially vertical interconnecting member indicated as 94 and 96 respectively to pivotally mount the cabinet 12 to one of the wall studs S. The upper and lower positioning assemblies 90 and 92 are similarly constructed. Specifically, the upper and lower positioning assemblies 90 and 92 each comprises a substantially L-shaped hinge member 98 coupled between a first pivot pin 100 coupled to a hinge element 102 affixed to the wall stud S and a substantially horizontally disposed flat hinge element 104 by a second pivot pin 106 that is, in turn, pivotally coupled to the cabinet 12 and mounting plate 108 by a third pivot pin 110. The substantially L-shaped hinge members 98 are interconnected by the first substantially vertical interconnecting member 94; while, the substantially horizontally disposed flat hinge elements 104 are interconnected by the second substantially vertical interconnecting member 96. The three pivot pins or points 100, 106 and 110 allow the cabinet 12 to be stored in the recess R formed in the wall W substantially parallel to the wall W and positioned substantially perpendicular to the wall W when in use.

As best shown in FIGS. 2 and 4, an access door 112 is hingedly coupled to the cabinet 12 by a hinge 114 to permit selective access to the disposal container or bin 32 which may be removably disposed with the lower portion of the cabinet 12.

Figure 9:
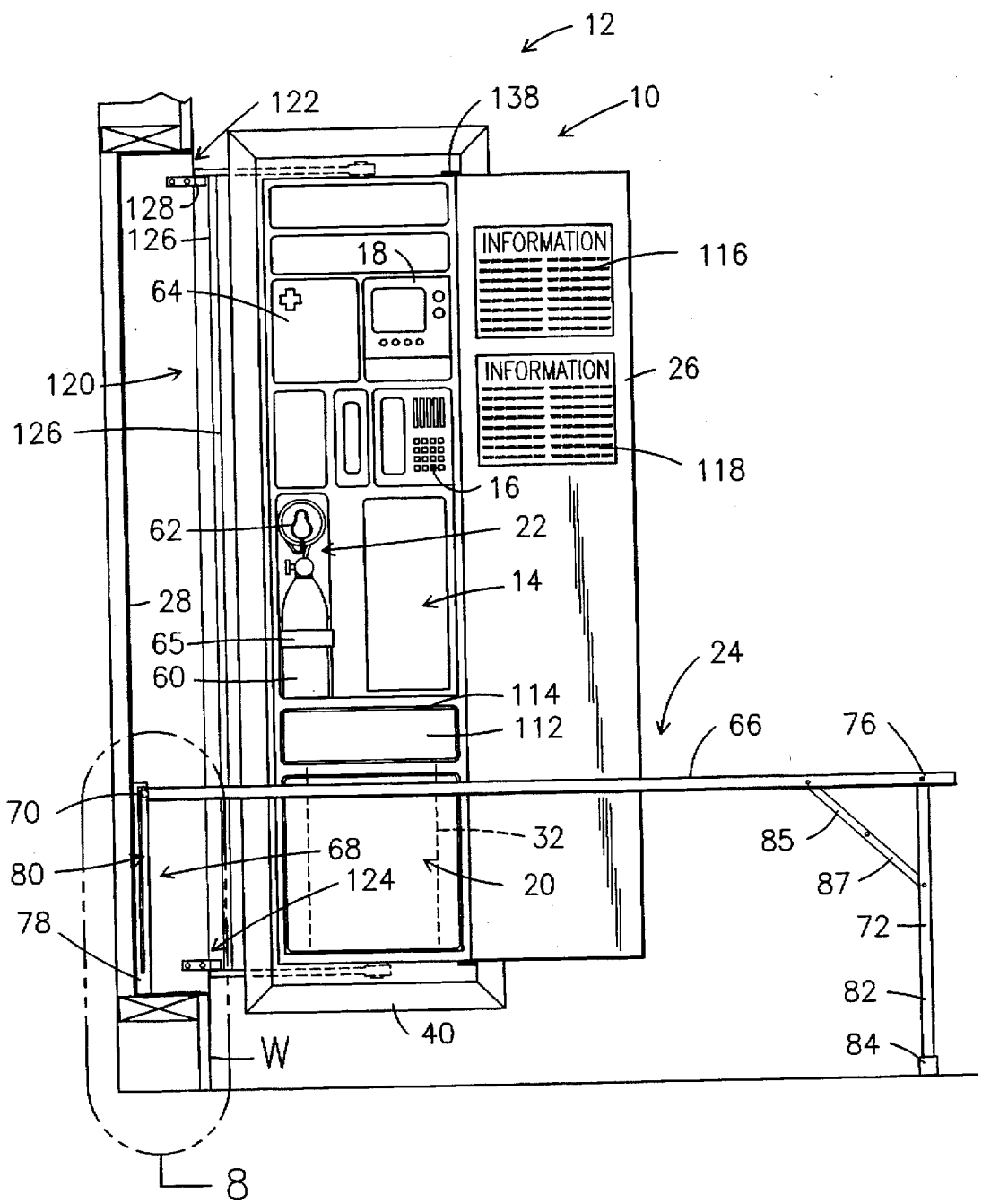
FIG. 9 is a partial side view of the integrated medical diagnostic center with an alternate positioning means.
Figure 10:
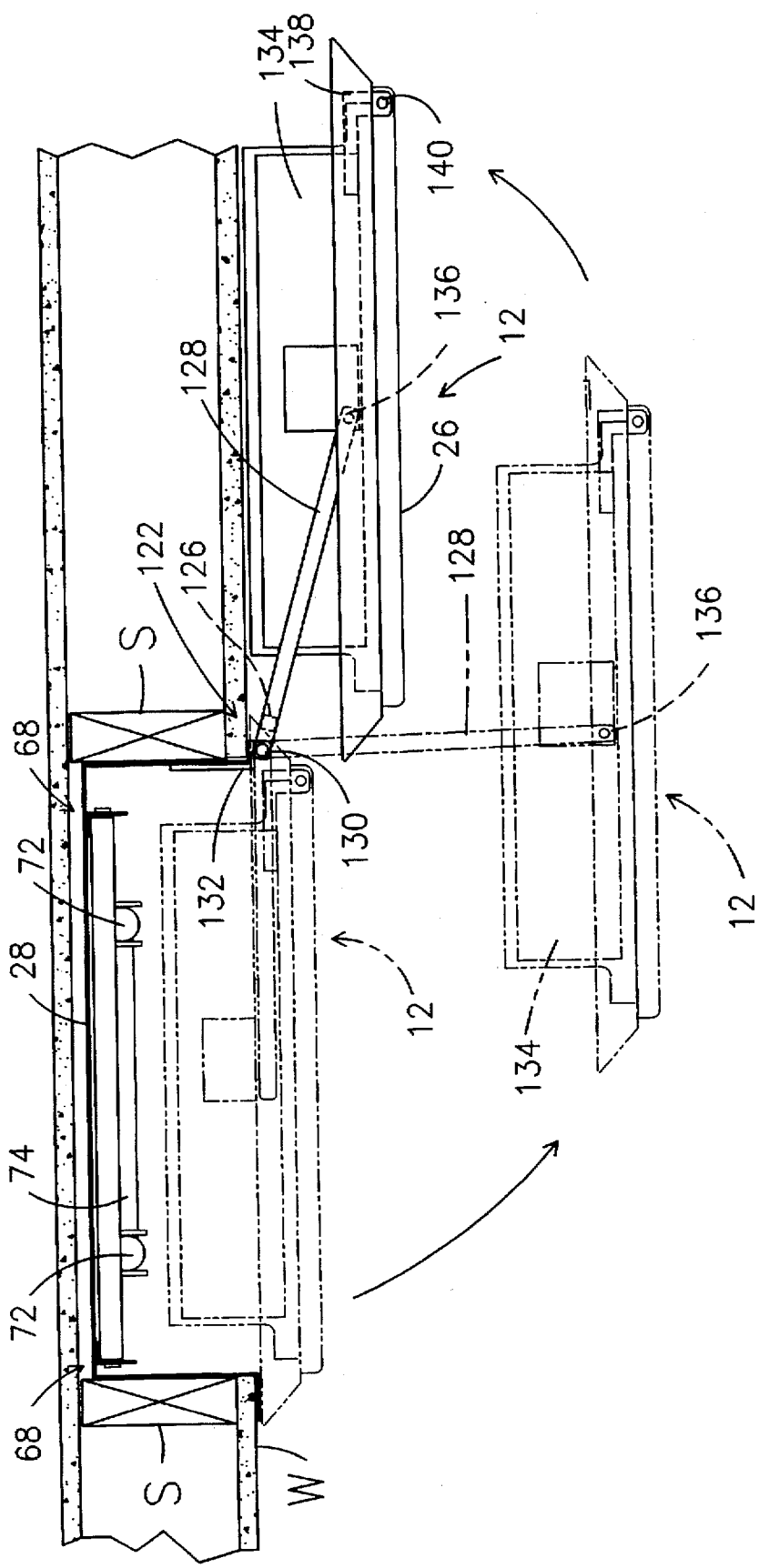
FIG. 10 is a top view of the integrated medical diagnostic medical center with the alternate positioning means with the cabinet in various positions.

FIGS. 9 and 10 show an alternate cabinet positioning means generally indicated as 120 comprising an upper and lower positioning assembly generally indicated as 122 and 124 respectively coupled together by a first substantially vertical interconnecting member 126 to pivotally mount the cabinet 12 to the wall W. The upper and lower positioning assemblies 122 and 124 are similarly constructed.

Specifically, the upper and lower positioning assemblies 122 and 124 each comprises a substantially horizontal hinge member 128 coupled between a first pivot pin 130 coupled to a hinge element 132 affixed to the wall W and a substantially horizontally disposed flat mounting plate 134 by a second pivot pin 136 affixed to the cabinet 12. A substantially L-shaped hinge member 138 is formed on to each substantially horizontally disposed flat mounting plate 134 and extends through the cabinet 12 to hingedly support the cabinet door 26 on hinge pins 140. The pivot pins or points 130 and 136 allow the cabinet 12 to be stored in the recess R formed in wall W substantially parallel to the wall W and positioned substantially parallel to the wall W in the extended or open position when in use.

The integrated medical diagnostic center 10 is disposed in the recess R when not in use. To use, the cabinet door 26 is opened to permit access to the emergency communications device 16, the diagnostic devices 18 and the first patient support 20.

With the cabinet door 26 in the open position (FIGS. 3 and 4), the first patient support 20 is opened or deployed to the operative position with the pair of seat supports 52 placed in the support ledges 56 formed on the opposite sides of the lower portion of the substantially vertical interior wall 34 to support the free ends 58 of the seat supports 52 to maintain the seat platform 44 in the operative or horizontal position.

With the person seated on the seat platform 44, the diagnostic devices 18 and the emergency treatment devices 22 are accessible for use on the patient.

As best shown in FIG. 5, with the cabinet door 26 and cabinet 12 in the open position, the second patient support 24 may be deployed or moved to the operative position such that the foot elements 82 maintain the platform 66 in the operative or horizontal position to permit the person to lie on the second patient support 24.

Emergency instructions and other medical or equipment information may be provided on the inside of the cabinet door 26 indicated as indicia 116 and 118 in FIG. 1.

It will thus be seen that the objects set forth above, among those made apparent from the preceding description are efficiently attained and since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described, what is claimed is:

1. An integrated medical diagnostic center for installation into a wall of a room configured to provide emergency communications, immediate measurement of various physiological conditions and administration of emergency treatment, said integrated medical diagnostic center comprising a cabinet having a peripheral side wall terminating in an outer flange having an inclined surface, said outer flange engaging the wall when the cabinet is in the closed position, said cabinet including a plurality of compartments to house an emergency communications device, a plurality of physiological diagnostic devices, at least one emergency treatment device and at least one patient support movable between a stored position and an operative position to support a patient when in the operative position.

2. The integrated medical diagnostic center of claim 1 wherein said cabinet further includes a substantially vertical interior wall contains a plurality of substantially horizontal elements extending outwardly from said substantially vertical interior wall to cooperatively form said compartments therebetween.

3. The integrated medical diagnostic center of claim 2 further comprising securing means affixed to said substantially vertical interior wall to selectively secure the emergency communications device, diagnostic devices and the emergency treatment device within said corresponding compartments.

4. The integrated medical diagnostic center of claim 3 wherein said securing means comprises a hook and loop combination.

5. The integrated medical diagnostic center of claim 1 further includes a second patient support movable between a stored position and an operative position, said second patient support comprising a platform movably coupled to a pair of side supports by a corresponding pivot member on each side of said platform and a pair of outer platform supports pivotally coupled to opposite sides of said platform.

6. The integrated medical diagnostic center of claim 5 wherein each said side support comprises a support member affixed to said cabinet including a substantially vertical J-shaped slot to receive said corresponding pivot member.

7. The integrated medical diagnostic center of claim 6 further comprising a foot element attached to the free ends of said platform supports to maintain said platform in an operative or horizontal position.

8. The integrated medical diagnostic center of claim 6 wherein said second patient support includes a first and second platform brace pivotally coupled to each other and to said platform and at least one of said outer platform supports.

9. The integrated medical diagnostic center of claim 5 further including a cabinet positioning means coupled between said cabinet and the wall structure to selectively move said cabinet between a closed position and an open position to expose said second patient platform.

10. The integrated medical diagnostic center of claim 9 wherein said cabinet positioning means comprises an upper and lower positioning assembly to pivotally mount said cabinet to the wall structure.

11. The integrated medical diagnostic center of claim 10 wherein said upper and lower positioning assembly each comprises a hinge member coupled between a first pivot pin coupled to a hinge element affixed to the wall structure and a hinge element by a second pivot pin pivotally coupled to said cabinet and a mounting plate by a third pivot pin.

12. The integrated medical diagnostic center of claim 11 wherein said hinge members are substantially L-shaped in configuration.

13. The integrated medical diagnostic center of claim 12 wherein said substantially L-shaped hinge members are interconnected by a first substantially vertical interconnecting member.

14. The integrated medical diagnostic center of claim 13 wherein said hinge elements are interconnected by a second substantially vertical interconnecting member.

15. The integrated medical diagnostic center of claim 11 wherein said hinge members are interconnected by a first substantially vertical interconnecting member and said hinge elements are interconnected by a second substantially vertical interconnecting member.

16. The integrated medical diagnostic center of claim 11 wherein said three pivot pins or points allow said cabinet to be stored in the recess formed in the wall substantially parallel to the wall and positioned substantially perpendicular to the wall when in use.

17. The integrated medical diagnostic center of claim 16 wherein said peripheral side wall terminates in an outer flange having an inclined surface, said outer flange engaging the wall when said cabinet is in the closed position.

18. The integrated medical diagnostic center of claim 2 further including a disposal container disposed within said cabinet.

19. The integrated medical diagnostic center of claim 18 further including an access door hingedly coupled to said cabinet to permit selective access to said disposal container.

20. The integrated medical diagnostic center of claim 19 wherein said disposal container is removably disposed with the lower portion of said cabinet.

21. The integrated medical diagnostic center of claim 9 further including a recess liner pan to receive said cabinet when in said closed position and house said second patient platform when in said stored position.

22. The integrated medical diagnostic center of claim 3 wherein said securing means comprises a strap and fastening means.

23. The integrated medical diagnostic center of claim 1 further including a cabinet door movable between an open and closed position to selectively conceal said compartments when in said closed position, said cabinet door including indicia for medical or equipment instruction.

24. An integrated medical diagnostic center for installation into a wall of a room configured to provide emergency communications, immediate measurement of various physiological conditions and administration of emergency treatment, said integrated medical diagnostic center comprising a cabinet including a plurality of compartments to house an emergency communications device, a plurality of physiological diagnostic devices, at least one emergency treatment device and at least one patient support comprising a seat platform pivotally coupled to said cabinet by a pivot means on opposite sides thereof and a pair of seat supports pivotally coupled to opposite sides of said seat platform on the outer portion thereof movable between a stored position and an operative position to support a patient when in the operative position.

25. An integrated medical diagnostic center for installation into a wall of a room configured to provide emergency communications, immediate measurement of various physiological conditions and administration of emergency treatment, said integrated medical diagnostic center comprising a cabinet including a plurality of compartments to house an emergency communications device, a plurality of physiological diagnostic devices, at least one emergency treatment device and at least one patient support movable between a stored position and an operative position to support a patient when in the operative position and a cabinet positioning means comprising an upper and lower positioning assembly to pivotally mount said cabinet to the wall coupled between said cabinet and the wall structure to selectively move said cabinet between a closed position and an open position.

26. The integrated medical diagnostic center of claim 25 wherein said upper and lower positioning assembly each comprises a hinge member coupled between a first pivot pin coupled to a hinge element affixed to the wall structure and mounting plate by a second pivot pin pivotally coupled to said cabinet.

27. The integrated medical diagnostic center of claim 26 further including substantially L-shaped hinge member interconnected to each said mounting plate to hingedly support an access door on said cabinet.

28. The integrated medical diagnostic center of claim 24 wherein support ledges are formed on opposite sides of the lower portion of said substantially vertical interior wall to selectively receive and support the free ends of said seat supports to maintain said seat platform in the operative position.

29. The integrated medical diagnostic center of claim 28 wherein said first patient support includes a first and second seat platform brace pivotally coupled to each other and to said seat platform and at least one of said seat supports.

* * * * *